United States Patent
Godek et al.

(10) Patent No.: US 9,381,170 B2
(45) Date of Patent: *Jul. 5, 2016

(54) CYCLOALKYL-DIAMINES FOR NEURODEGENERATIVE DISORDERS

(71) Applicants: Dennis Michael Godek, Glastonbury, CT (US); Harry Ralph Howard, Bristol, CT (US)

(72) Inventors: Dennis Michael Godek, Glastonbury, CT (US); Harry Ralph Howard, Bristol, CT (US)

(73) Assignee: MediSynergics, LLC, Newington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/811,287

(22) Filed: Jul. 28, 2015

(65) Prior Publication Data

US 2016/0151308 A1  Jun. 2, 2016

Related U.S. Application Data

(63) Continuation-in-part of application No. 14/167,362, filed on Jan. 29, 2014, now Pat. No. 9,126,891.

(60) Provisional application No. 61/758,538, filed on Jan. 30, 2013.

(51) Int. Cl.

| | |
|---|---|
| A61K 31/426 | (2006.01) |
| A61K 31/41 | (2006.01) |
| A61K 31/4196 | (2006.01) |
| A61K 31/417 | (2006.01) |
| A61K 31/131 | (2006.01) |
| A61K 31/138 | (2006.01) |
| A61P 9/10 | (2006.01) |
| A61P 25/28 | (2006.01) |
| A61K 31/135 | (2006.01) |
| A61K 31/341 | (2006.01) |
| A61K 31/4409 | (2006.01) |
| A61K 31/40 | (2006.01) |
| A61K 31/5375 | (2006.01) |
| A61K 31/495 | (2006.01) |
| C07D 233/64 | (2006.01) |
| C07D 249/08 | (2006.01) |
| C07D 257/04 | (2006.01) |
| C07D 277/28 | (2006.01) |
| C07D 277/64 | (2006.01) |
| C07C 211/37 | (2006.01) |
| C07C 211/36 | (2006.01) |
| C07C 217/74 | (2006.01) |

(52) U.S. Cl.
CPC .............. *A61K 31/135* (2013.01); *A61K 31/341* (2013.01); *A61K 31/40* (2013.01); *A61K 31/417* (2013.01); *A61K 31/4409* (2013.01); *A61K 31/495* (2013.01); *A61K 31/5375* (2013.01)

(58) Field of Classification Search
CPC .. C07D 233/64; C07D 249/08; C07D 257/04; C07D 277/28; C07D 277/64; C07C 211/37; C07C 211/36; C07C 217/74
USPC ...................... 514/237.8, 357, 406, 471, 647; 544/165; 546/329; 548/335.5; 549/492; 564/307
See application file for complete search history.

(56) References Cited

U.S. PATENT DOCUMENTS

| | | | |
|---|---|---|---|
| 2009/0005456 A1 * | 1/2009 | Shao ...................... | C07C 215/42 514/650 |
| 2014/0221473 A1 * | 8/2014 | Amin ..................... | C07C 323/30 514/462 |

FOREIGN PATENT DOCUMENTS

FR    WO 2006048546 A1 *   5/2006   .............. C07B 53/00

OTHER PUBLICATIONS

Nguyen, L et al "Role of sigma-1 receptors in neurodegenerative diseases" Journal of Pharmacological Sciences (2015), 127:17-29.
Ruscher, K et al "The sigma-1 receptor enhances brain plasticity and functional recovery after experimental stroke" Brain (2011), 134: 732-746.
Schetz, JA et al "A prototpical Sigma-1 receptor antagonist protects against brain ischemia" Brain Research (2007), 1181:1-9.
Urfer, R et al "Phase II Trial of the Sigma-1 Receptor Agonist Cutamesine (SA4503) for Recovery Enhancement After Acute Ischemic Stroke" (2014) 45:3304-3310.

* cited by examiner

*Primary Examiner* — Nyeemah A Grazier
*Assistant Examiner* — Amanda L Aguirre

(57) ABSTRACT

The invention is directed to the use of a compound of formula I as defined herein, a pharmaceutically acceptable salt thereof; or a pharmaceutical composition containing a compound of formula I, in treating a mammal, including a human, for a psychiatric disorder or condition selected from the group consisting of stroke, Huntington's disease and amyotrophic lateral sclerosis (ALS).

6 Claims, No Drawings

CYCLOALKYL-DIAMINES FOR NEURODEGENERATIVE DISORDERS

This U.S. patent application claims the benefit of U.S. Provisional Application No. 61/758,538 filed Jan. 30, 2013 and U.S. Non-Provisional application Ser. No. 14/167,362 filed on Jan. 29, 2014.

BACKGROUND OF THE INVENTION

This invention is directed to compounds of the formula I as described herein, to a pharmaceutical composition comprising such compounds and to methods of treating disorders or conditions that may be treated by administration of such compounds to a mammal in need, including humans. In particular, the compounds of the current invention are potentially useful for treating stroke, Huntington's disease and amyotrophic lateral sclerosis (ALS).

Neurodegeneration refers to the progressive loss of structure or function, including death, of neurons. Neurodegenerative diseases include ALS (amyotrophic lateral sclerosis), Parkinson's, Alzheimer's, and Huntington's diseases and occur as a result of neurodegenerative processes. They are incurable, resulting in progressive degeneration and/or death of neuron cells.

Amyotrophic lateral sclerosis (ALS), also known as Lou Gehrig's disease and Charcot disease, is a specific disorder that involves the death of neurons. ALS is characterized by stiff muscles, muscle twitching, and gradually worsening weakness due to muscle wasting. This results in difficulty speaking, swallowing, and eventually impairs breathing.

ALS is classified as a rare disease, but is the most common motor neuron disease. People of all races and ethnic backgrounds are affected. The cause is not known in 90% to 95% of cases. About 5-10% of cases are inherited from a person's parents. About half of these genetic cases are due to one of two specific genes. It results in the death of the neurons that control voluntary muscles. The diagnosis is based on a person's signs and symptoms with testing done to rule out other potential causes.

There is no cure for ALS. A medication called riluzole may extend life expectancy by about two to three months. Non-invasive ventilation may result in both improved quality and length of life. The disease usually starts around the age of 60 and in inherited cases around the age of 50. The average survival from onset to death is three to four years. About 10% survive longer than 10 years. Most die from respiratory failure. In much of the world, rates of ALS are unknown. In Europe, the disease affects about 2.2 people per 100,000 per year. In the United States, more than 5,600 are diagnosed every year, and up to 30,000 Americans are currently affected. ALS is responsible for two deaths per 100,000 people per year.

Huntington's disease (HD) is a neurodegenerative genetic disorder that affects muscle coordination and leads to mental decline and behavioral symptoms. Symptoms of the disease can vary between individuals and affected members of the same family, but usually progress predictably. The earliest symptoms are often subtle problems with mood or cognition. A general lack of coordination and an unsteady gait often follows. As the disease advances, uncoordinated, jerky body movements become more apparent, along with a decline in mental abilities and behavioral symptoms. Physical abilities gradually worsen until coordinated movement becomes difficult. Mental abilities generally decline into dementia. Complications such as pneumonia, heart disease, and physical injury from falls reduce life expectancy to around twenty years from the point at which symptoms begin.

Physical symptoms can begin at any age from infancy to old age, but usually begin between 35 and 44 years of age. The disease may develop earlier in life in each successive generation. About 6% of cases start before the age of 21 years with an akinetic-rigid syndrome; they progress faster and vary slightly. The variant is classified as juvenile, akinetic-rigid, or Westphal variant HD. The late onset of Huntington's disease means it does not usually affect reproduction.

The worldwide prevalence of HD is 5-10 cases per 100,000 persons, but varies greatly geographically as a result of ethnicity, local migration and past immigration patterns. Prevalence is similar for men and women. The rate of occurrence is highest in peoples of Western European descent, averaging around 7 per 100,000 people, and is lower in the rest of the world; e.g., one per million people of Asian and African descent. A 2013 epidemiological study of the prevalence of Huntington's disease in the U.K. between 1990 and 2010 found that the average prevalence for the U.K. was 12.3 per 100,000.

HD is the most common genetic cause of abnormal involuntary writhing movements called chorea, which is why the disease used to be called Huntington's chorea. The disease is caused by an autosomal dominant mutation in either of an individual's two copies of a gene called Huntingtin.

There is no cure for HD, and full-time care is required in the later stages of the disease. Existing pharmaceutical and non-drug treatments can relieve many of its symptoms. It is much more common in people of Western European descent than in those of Asian or African ancestry. The disease can affect both men and women.

Tetrabenazine was approved in 2008 for treatment of chorea in Huntington's disease in the US. Other drugs that help to reduce chorea include neuroleptics and benzodiazepines. Compounds such as amantadine or remacemide are still under investigation but have shown preliminary positive results. Hypokinesia and rigidity, especially in juvenile cases, can be treated with antiparkinsonian drugs, and myoclonic hyperkinesia can be treated with valproic acid.

Stroke, also known as cerebrovascular accident (CVA), cerebrovascular insult (CVI), or brain attack, occurs when poor blood flow to the brain results in cell death. There are two main types of stroke: ischemic due to lack of blood flow and hemorrhagic due to bleeding. They result in part of the brain not functioning properly. Signs and symptoms of a stroke may include an inability to move, problems understanding or speaking, and loss of vision to one side. Signs and symptoms often appear soon after the stroke has occurred. If symptoms last less than one or two hours it is known as a transient ischemic attack (TIA). Hemorrhagic strokes may also be associated with a severe headache. The symptoms of a stroke can be permanent. Long term complications may include pneumonia or loss of bladder control.

Prevention includes decreasing risk factors as well as possibly aspirin, statins, surgery to open up the arteries to the brain in those with problematic narrowing, and warfarin in those with atrial fibrillation. A stroke often requires emergency care. An ischemic stroke, if detected within three to four and half hours, may be treatable with a medication that can break down the clot. Aspirin should be used. Some hemorrhagic strokes benefit from surgery. Treatment to try recover lost function is called rehabilitation and ideally takes place in a stroke unit; however, these are not available in much of the world.

In 2010, approximately 17 million people had a stroke and 33 million people had previously had a stroke and were still alive. Between 1990 and 2010 the number of strokes which occurred each year decreased by approximately 10% in the developed world and increased by 10% in the developing world. In 2013, stroke was the second most frequent cause of death after coronary artery disease, accounting for 6.4 million deaths (12% of the total). About 3.3 million deaths resulted from ischemic stroke while 3.2 million deaths resulted from hemorrhagic stroke. About half of people who have had a stroke live less than one year. Overall, two thirds of strokes occurred in those over 65 years old.

Recently, there has been increased awareness of the potential for compounds which function as sigma-1 receptor ligands. The structure and functions of the "receptor" have been described in a variety of publications (e.g., Duncan G and Wang L (2005) *Experimental Eye Research*, 81:121-122; Ortega-Roldan J L, Ossa F, Schnell J R (2013) *Journal of Biological Chemistry*, 288(29):21448-21457; Monnet F P (2005) *Biol. Cell* 97:873-883 (doi:10.1042/BC20040149); Ishikawa M, Hashimoto K (2010) *Journal of Receptor, Ligand and Channel Research*, 3:25-36)

In a paper by Nguyen, et al (Nguyen L, Lucke-Wold B P, Mookerjee S A Cavendish J Z, Robson M J, Scandinaro A L and Matsumoto R R, *Journal of Pharmacological Sciences* (2015) 127:17-29), the mechanisms of neurodegeneration and the potential for the use of highly selective sigma-1 receptor ligands is discussed in great detail. They describe the mechanisms by which drugs that interact with the sigma-1 receptor may confer neuroprotection, including calcium homeostasis, attenuation of reactive species (e.g., NO) production, modulation of endoplasmic reticulum (ER) and mitochondrial function and modulation of glial activity. Because of these capabilities, they postulate that sigma-1 ligands may have beneficial effects in the treatment of stroke, ALS and Huntington's diseases.

In animal studies, rats treated with the sigma-1 agonist 1-(3,4-dimethoxyphenethyl)-4-(3-phenylpropyl)piperazine dihydrochloride within two days of induced ischemic injury showed enhanced recovery of lost sensorimotor function without decreasing infarct size, suggesting that sigma-1 activation stimulates recovery after stroke by stimulating brain plasticity (Ruscher K, Shamloo M, Rickhag M, Ladunga I, Soriano L, et al (2011) *Brain*; doi:10.1093/brain/awq367). A sigma-1 selective antagonist, BD1063, as well as the potent antipsychotic drug haloperidol (also a potent sigma-1 antagonist) also showed neuroprotective activity at low doses when administered acutely as a protective agent against cerebral ischemic stroke in in vivo animal studies (Schetz J A, Perez E, Liu R, Chen S, Lee I and Simpkins J W (2007) Brain Research, 1181:1-9; doi:10.1016/j.brainres.2007.08.068)

For example, the sigma-1 agonist cutamesine (SA4503) was recently studied in a Phase 2 trial with a group of 60 patients suffering from ischemic stroke (Urfer R, Moebius H J, et al (2014) *Stroke*, 45:3304-3310). No adverse effects were observed and additional studies were planned.

The present invention relates to the use of novel cycloalkyl-diamines and to their pharmaceutical compositions in the treatment of neurodegenerative disorders from the group consisting of stroke, Huntington's disease and amyotrophic lateral sclerosis (ALS) in mammals, including humans. Many of the compounds disclosed in this application exhibit significant affinity as sigma-1 ligands.

SUMMARY OF THE INVENTION

The present invention is directed to a method for the treatment of psychiatric disorders in mammals, including humans, by administering a compound of the formula I, or a pharmaceutically effective salt(s) thereof, in an amount which is effective in the treatment of neurodegenerative disorders from the group consisting of stroke, Huntington's disease and amyotrophic lateral sclerosis (ALS) in mammals, wherein:

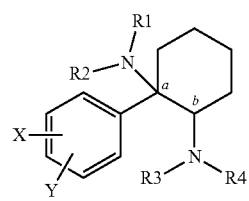

X and Y are independently selected from the group consisting of H, F, Cl, Br, I, CN, OH, $CF_3$, $C_2F_5$, $C_1$-$C_6$-alkyl, $C_3$-$C_7$-cycloalkyl, $C_1$-$C_3$-alkoxy, aryl, heteroaryl, —(—C=O)—R5, —NH—(C=O)—R5, —NR5-(C=O)—R6, —(C=O)—NHR5 and —(C=O)—NR5R6;

R1 is hydrogen;

R2 is hydrogen or $C_1$-$C_6$-alkyl;

R3 is hydrogen or $C_1$-$C_6$-alkyl;

R4 is selected from the group consisting of $C_1$-$C_6$-alkyl, $C_3$-$C_7$-cycloalkyl, $(CH_2)_n$-R7, or NR3R4 is a 5- to 12-membered cyclic or bicyclic ring system containing up to two additional heteroatoms in the ring, selected from N, O and S;

R5 is selected from $C_1$-$C_6$-alkyl and aryl;

R6 is selected from $C_1$-$C_6$-alkyl and aryl, or

NR5R6 is a 5- to 12-membered cyclic or bicyclic ring system containing up to two additional heteroatoms in the ring, selected from N, O and S;

R7 is independently selected from the group consisting of H, $C_1$-$C_6$-alkyl, $C_3$-$C_7$-cycloalkyl, $(C_1$-$C_6$-alkyloxy)-, $(C_1$-$C_6$-alkyloxy)-$(C_1$-$C_6$-alkyl)-, NR8R9-, NR8R9-$(C_1$-$C_6$-alkyl), aryl, heterocyclyl and heteroaryl;

R8 and R9 are independently selected from hydrogen, $C_1$-$C_6$-alkyl and aryl, or taken together with the N atom to which they are attached form a 3- to 8-membered ring containing up to two additional heteroatoms, selected from N, O and S; and n is an integer between 0 and 6.

Preferred embodiments of the present invention include the compounds of formula I in which:

(A) R2 is methyl, R1 and R3 are hydrogen, Y is hydrogen;
  X is halogen;
  n is an integer between 0 to and 6; and
  R7 is aryl or heteroaryl.

(B) R2 is methyl, R1 and R3 are hydrogen; Y is hydrogen;
  X is halogen;
  n is an integer between 0 to and 6; and
  R7 is heterocyclyl.

(C) R2 is methyl; R1 and R3 are hydrogen; Y is hydrogen;
  X is halogen;
  n is an integer between 0 to and 6; and
  R7 is NR8R9.

Preferred compounds of formula I in accordance with the present invention include:
  trans-1-(2-chlorophenyl)-$N^2$-(2-(dimethylamino)ethyl)-$N^1$-methylcyclohexane-1,2-diamine;
  cis-1-(2-chlorophenyl)-$N^2$-(2-(dimethylamino)ethyl)-$N^1$-methylcyclohexane-1,2-diamine;
  trans-1-(2-chlorophenyl)-$N^2$-cyclopropyl-$N^1$-methylcyclohexane-1,2-diamine;

cis-1-(2-chlorophenyl)-N²-cyclopropyl-N¹-methylcyclohexane-1,2-diamine;
trans-1-(2-chlorophenyl)-N²-cyclopentyl-N¹-methylcyclohexane-1,2-diamine;
cis-1-(2-chlorophenyl)-N²-cyclopentyl-N¹-methylcyclohexane-1,2-diamine;
trans-1-(2-chlorophenyl)-N²-(3-methoxypropyl)-N¹-methylcyclohexane-1,2-diamine;
cis-1-(2-chlorophenyl)-N²-(3-methoxypropyl)-N¹-methylcyclohexane-1,2-diamine;
trans-1-(2-chlorophenyl)-N¹-methyl-N²-(tetrahydrofuran-2-ylmethyl)cyclohexane-1,2-diamine;
cis-1-(2-chlorophenyl)-N¹-methyl-N²-(tetrahydrofuran-2-ylmethyl)cyclohexane-1,2-diamine;
cis-1-(2-chloropheny)-N²-(3-(dimethylamino)propyl)-N¹-methylcyclohexane-1,2-diamine;
trans-N²-benzyl-1-(2-chlorophenyl)-N¹-methylcyclohexane-1,2-diamine;
cis-N²-benzyl-1-(2-chlorophenyl)-N¹-methylcyclohexane-1,2-diamine;
cis-1-(2-chlorophenyl)-N¹-methyl-N²-(pyridin-4-ylmethyl)cyclohexane-1,2-diamine;
trans-1-(2-chlorophenyl)-N¹-methyl-N²-(pyridin-3-ylmethyl)cyclohexane-1,2-diamine;
cis-1-(2-chlorophenyl)-N²-(1-(R)-phenyl)-ethyl)-N¹-methylcyclohexane-1,2-diamine;
trans-1-(2-chlorophenyl)-N²-(1-(S)-phenyl)-ethyl)-N¹-methylcyclohexane-1,2-diamine;
trans-1-(2-chlorophenyl)-N²-(3-(1-imidazolyl)-propyl)-N¹-methylcyclohexane-1,2-diamine;
cis-1-(2-chlorophenyl)-N²-(3-(1-imidazolyl)-propyl)-N¹-methylcyclohexane-1,2-diamine;
trans-1-(2-chlorophenyl)-N²-(1-ethyl-pyrrolidin-2-ylmethyl)-N¹-methylcyclohexane-1,2-diamine;
cis-1-(2-chlorophenyl)-N²-(1-ethyl-pyrrolidin-2-ylmethyl)-N¹-methylcyclohexane-1,2-diamine;
trans-1-(2-chlorophenyl)-N²-(3-(pyrrolidin-1-yl)propyl)-N¹-methylcyclohexane-1,2-diamine;
cis-1-(2-chlorophenyl)-N²-(3-(pyrrolidin-1-yl)propyl)-N¹-methylcyclohexane-1,2-diamine;
trans-1-(2-chlorophenyl)-N²-(3-phenylpropyl)-N¹-methylcyclohexane-1,2-diamine;
cis-1-(2-chlorophenyl)-N²-(3-phenylpropyl)-N¹-methylcyclohexane-1,2-diamine;
trans-1-(2-chlorophenyl)-N²-(3-(morpholin-1-yl)propyl)-N¹-methylcyclohexane-1,2-diamine;
cis-1-(2-chlorophenyl)-N²-(3-(morpholin-1-yl)propyl)-N¹-methylcyclohexane-1,2-diamine;
trans-1-(2-chlorophenyl)-N²-(3-(4-methylpiperazin-1-yl)propyl)-N¹-methylcyclohexane-1,2-diamine;
cis-1-(2-chlorophenyl)-N²-(3-(4-methylpiperazin-1-yl)propyl)-N¹-methylcyclohexane-1,2-diamine;
trans-1-(2-chlorophenyl)-N²-cyclohexyl-N¹-methylcyclohexane-1,2-diamine; and
cis-1-(2-chlorophenyl)-N²-cyclohexyl-N¹-methylcyclohexane-1,2-diamine.

Other compounds of the invention include the following:
1-(2-chloro-4-methoxyphenyl)-N²-[3-(4,5-dimethyl-1H-imidazol-2-yl)propyl]-N¹-methyl-cyclohexane-1,2-diamine;
1-(2-chlorophenyl)-N¹-methyl-N²-[3-(1H-1,2,4-triazol-5-yl)propyl]-cyclohexane-1,2-diamine;
1-(2-methylphenyl)-N¹-methyl-N²-[3-(3-methyl-1H-1,2,4-triazol-5-yl)propyl]-cyclohexane-1,2-diamine;
1-(2,4-dichlorophenyl)-N¹-methyl-N²-[3-(1H-tetrazol-5-yl)propyl]-cyclohexane-1,2-diamine;
1-(3,4-fluorophenyl)-N¹-methyl-N²-[2-(1-methyl-1H-tetrazol-5-yl)ethyl]-cyclohexane-1,2-diamine;
1-(4-chlorophenyl)-N²-(2-(dimethylamino)ethyl)-N¹-methylcyclohexane-1,2-diamine;
1-(2,4-dichlorophenyl)-N²-(2-(dimethylamino)ethyl)-N¹-methylcyclohexane-1,2-diamine;
1-(3,4-difluorophenyl)-N²-(2-(dimethylamino)ethyl)-N¹-methylcyclohexane-1,2-diamine;
1-(4-isopropylphenyl)-N²-(2-(dimethylamino)ethyl)-N¹-methylcyclohexane-1,2-diamine;
1-(2-methoxyphenyl)-N²-(2-(dimethylamino)ethyl)-N¹-methylcyclohexane-1,2-diamine;
1-(2-chlorophenyl)-N²-(2-(dimethylamino)ethyl)-N¹-methylcyclohexane-1,2-diamine;
1-(2-chlorophenyl)-N²-[3-(1H-imidazol-2-yl)propyl]-N¹-methylcyclohexane-1,2-diamine;
1-(2-chlorophenyl)-N²-[2-(1H-imidazol-2-yl)ethyl]-N¹-methylcyclohexane-1,2-diamine;
1-(2-chlorophenyl)-N¹-methyl-N²-[3-(1,3-thiazol-2-yl)propyl]-cyclohexane-1,2-diamine;
1-(3,5-dimethyl-2-chlorophenyl)-N¹-methyl-N²-[3-(1,3-thiazol-2-yl)propyl]-cyclohexane-1,2-diamine;
1-(3,5-dimethyl-phenyl)-N¹-methyl-N²-[3-(4,5-dimethyl-1,3-thiazol-2-yl)propyl]-cyclohexane-1,2-diamine;
1-(2-chlorophenyl)-N²-[3-(1,3-benzothiazol-2-yl)propyl]-N¹-methylcyclohexane-1,2-diamine;
1-(2,3-dichlorophenyl)-N²-[3-(1,3-benzimidazol-2-yl)propyl]-N¹-methylcyclohexane-1,2-diamine;
1-(3,4-dichlorophenyl)-N²-(2-(3,4-difluorophenyl)ethyl)-N¹-methylcyclohexane-1,2-diamine;
1-(2-chlorophenyl)-N²-(3-(3,4-difluorophenyl)propyl)-N¹-methylcyclohexane-1,2-diamine;
1-(2-chlorophenyl)-N²-(3-(4-fluorophenypropyl)-N¹-methylcyclohexane-1,2-diamine;
1-(2-chlorophenyl)-N²-(3-(3,4-dichlorophenyl)propyl)-N¹-methylcyclohexane-1,2-diamine;
1-(2-chlorophenyl)-N²-(3-(3,4-dimethoxyphenyl)propyl)-N¹-methylcyclohexane-1,2-diamine;
1-(2-chlorophenyl)-N²-[(4,5-dimethyl-1H-imidazol-2-yl)methyl]-N¹-ethylcyclohexane-1,2-diamine; and
1-(2-chlorophenyl)-N¹-ethyl-N²-[(1-methyl-1H-imidazol-2-yl)methyl]cyclohexane-1,2-diamine.

DETAILED DESCRIPTION OF THE INVENTION

The compounds of formula I may be prepared as described in the following reaction schemes and discussions. Unless otherwise indicated, X, Y, R1, R2, R3, R4, R5, R6, R7 and structural formulae II, III, IV, V, VI, VII, VIII, IX, X, XI, XII, XIII, XIV and XV in the reaction schemes and discussion that follow are defined as above.

Scheme 1

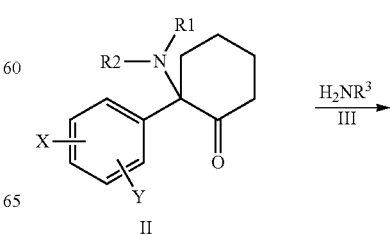

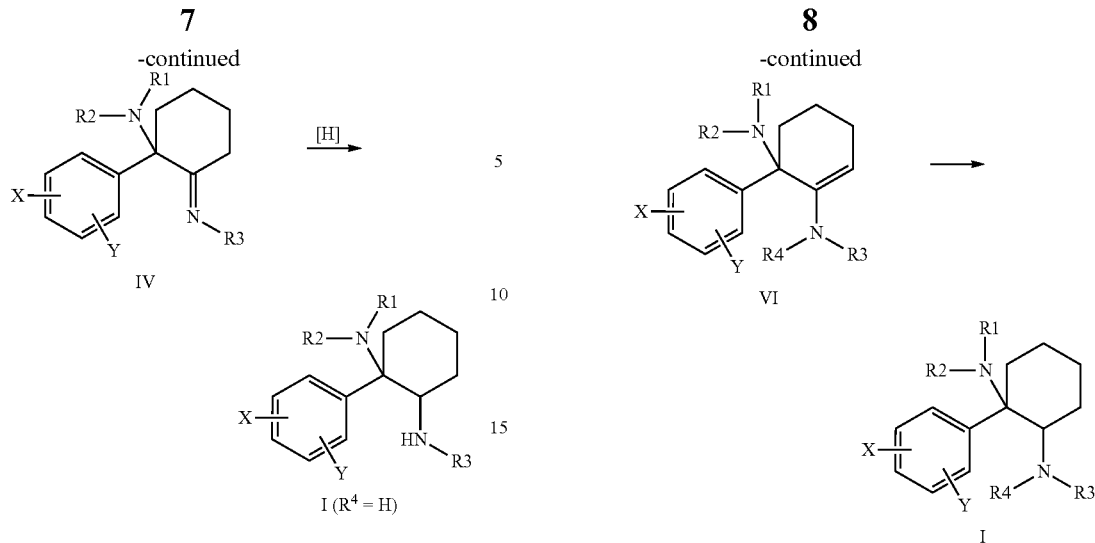

According to Scheme 1, a ketone of the general formula II, wherein X, Y, $R^1$ and $R^2$ are as previously defined, may be converted directly into the corresponding compound of the formula I, via an intermediate of the general formula IV, by reacting it with one or more equivalents of an primary amine of the general formula III in the presence of a reducing reagent. Reducing reagents that may be used include sodium cyanoborohydride, sodium triacetoxyborohydride, sodium borohydride, lithium aluminum hydride, hydrogen plus a metal catalyst, zinc plus hydrochloric acid, and formic acid. This reaction is typically conducted in a reaction inert solvent at a temperature from about 0° C. to about 150° C., but may be conducted in the absence of solvent. Suitable reaction inert solvents include lower alcohols (e.g., methanol, ethanol, isopropanol), 1,2-dichloroethane, acetic acid and tetrahydrofuran (THF)). Preferably the reaction is conducted with an excess of the corresponding amine III, in the absence of additional solvent, at a temperature of about 110° C., and using the reducing agent sodium cyanoborohydride.

Alternatively, the reaction of a compound of formula II with an amine compound of the formula III may be carried out in the presence of a dehydrating agent (e.g., titanium tetrachloride) or by using an apparatus designed to azeotropically remove the water generated, to produce an imine of the formula IV. This imine may then be converted to the title product of formula I by reduction of the C═N bond with a reducing agent as described above, preferably with sodium cyanoborohydride in the presence or absence of a suitable, reaction inert solvent as described in the preceding paragraph at a temperature of about 0° C. to about 150° C. and preferably at about 110° C. Other suitable dehydrating agents/solvent systems include titanium tetrachloride in dichloromethane, titanium isopropoxide in dichloromethane and activated molecular sieves in toluene or in dichloromethane.

When a secondary amine of the general formula V (i.e., HNR3R4) is used, an alternative method involves the formation of an enamine of general formula VI, which can be reduced to the title product of formula I through the use of a selective reducing agent or selective reduction conditions known to one familiar with the art of organic synthesis. Using this procedure, as shown in Scheme 2 above, the intermediate enamine VI may be isolated and purified if it is stable, or it may be used directly in the reduction step to generate the diamine of general formula I. Selective reducing agents and reagents to facilitate the conversion of intermediate VI to the compounds of formula I include: formic acid, hydrogen gas and a metal catalyst (e.g., Pd on carbon, Pt on carbon).

In another method (Scheme 3) for the preparation of the compounds of the present invention, an intermediate oxime (VII) can be prepared through reaction of the starting ketone I and hydroxylamine. Synthesis of such oximes is well precedented in the chemical literature (e.g., see LaMattina J L, et al, *Synthesis* (1980) 329-330), and it is also known that intermediate oximes like VII are capable of forming two different isomers, denoted as Z- and E-oximes. These isomers Scheme 3

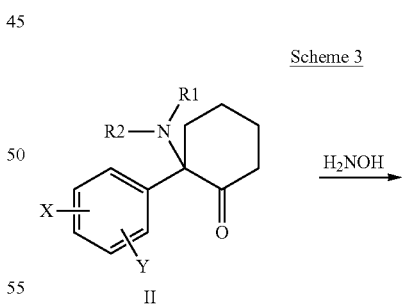

Scheme 2

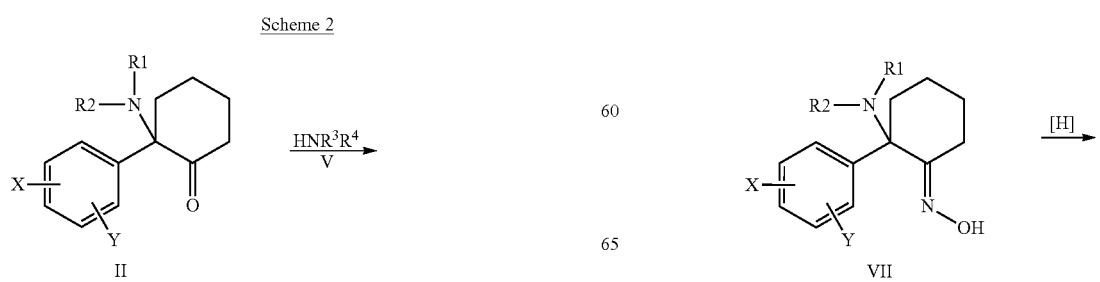

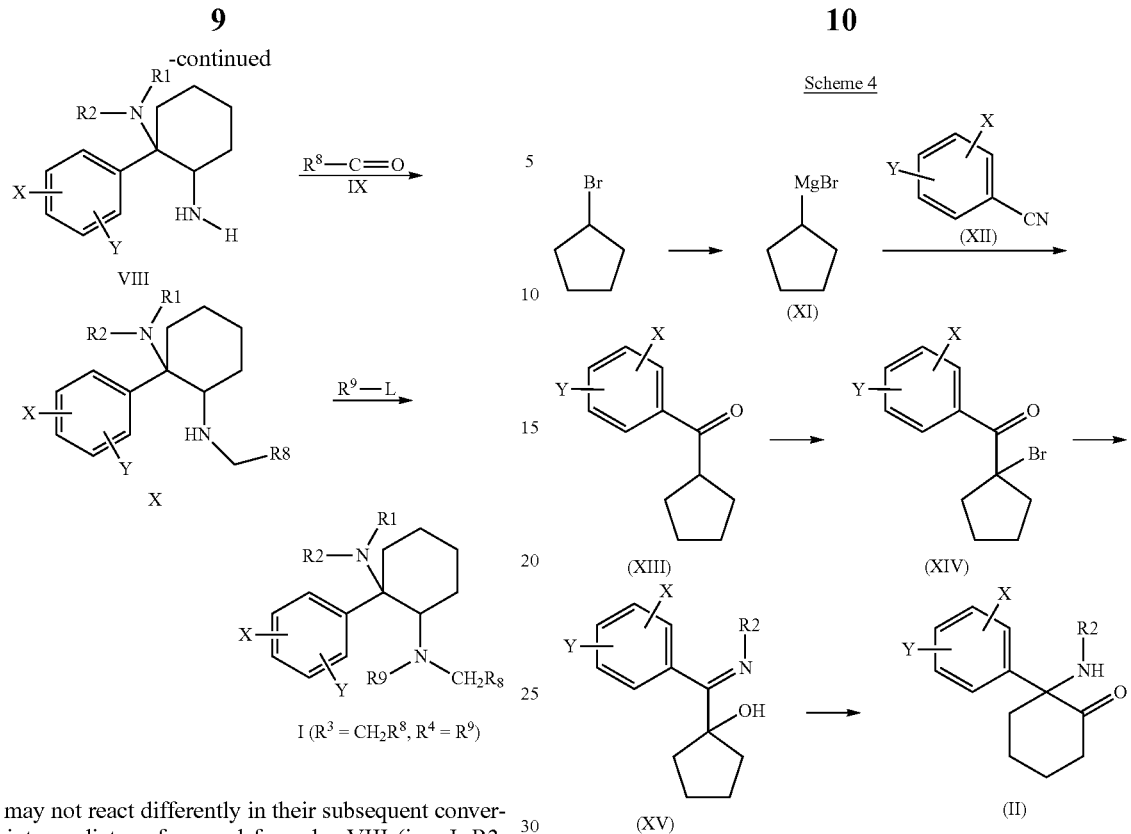

Scheme 4 may or may not react differently in their subsequent conversion to intermediates of general formulae VIII (i.e., I, R3, R4=H), and one of the oxime isomers may be less reactive or resistant to reduction to intermediate VIII. The reduction to VIII can be achieved using one of a variety of reagents and procedures, including Zn—AcOH, Na and $C_2H_5OH$, $BH_3$, and $NaBH_3CN$—$TiCl_3$.

In the next step, compound VIII can be converted to a compound of general formula X by subjecting it to a reductive amination with an aldehyde of general formula IX (for examples, see Jerry March, "Advanced Organic Chemistry: Reactions, Mechanisms and Structure", $4^{th}$ Ed., John Wiley & Sons, New York, N.Y. (1992) pp 898-900) followed by alkylation of the nitrogen atom of the intermediate of general formula X with a reagent of general formula R9-L, where L is a leaving group (e.g., Cl, Br, mesylate) and R9 is $C_1$-$C_3$ alkyl. Procedures for these reactions are readily available in the chemical literature and familiar to chemists with skill in the art of organic synthesis.

The starting ketone for the above processes, compound II, may be obtained from commercial sources or may be synthesized as described in the chemical literature (Scheme 4). Such compounds may exist as racemic mixtures or as the individual (+)- and (−)-isomers.

In general, 1-bromo-cyclopentane is converted to a Grignard reagent (XI) by reaction with magnesium metal in an inert solvent, typically in ethers like diethyl ether or tetrahydrofuran (THF). The Grignard reagent so formed is then reacted with an appropriately substituted arylnitrile (XII), in an inert solvent such as hexane, and stirred at room temperature until the reaction is determined to have been completed. The product, the arylketone (XIII), dissolved in a suitable solvent (e.g., chloroform) is then treated with one equivalent of bromine ($Br_2$), and the resulting α-bromo-ketone (XIV) is isolated by filtration. Compound XIV is then added to a primary amine of general formula $R2$-$NH_2$ in an inert solvent (e.g., toluene) and the mixture is heated to reflux. The solvents are subsequently removed under vacuum to obtain the crude α-hydroxy-imine (XV). This intermediate is then heated, typically in a high-boiling, inert solvent (e.g., decalin) wherein the compound undergoes a thermal rearrangement to produce the α-amino-ketone (II).

Specifically, the compound II in which X is 2-chloro, Y is H, R1 is hydrogen and R2 is methyl is commonly referred to as ketamine. Ketamine is a Central Nervous System active drug that may interact with NMDA (i.e., N-Methyl-D-Aspartate) receptors in the brain and has been associated with a variety of behavioral disorders in human and animal studies. The synthesis and utility of ketamine and related analogs as NMDA receptor modulators and disease treatments are described by T. G. Gant and S. Sarshar in US Patent Application 2008/109958 (Apr. 25, 2008).

The compounds of the present invention may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

Where cis- and trans-isomers are possible (i.e., at positions "a" and "b" in structure formula I), for an embodiment of the inventive compounds of formula I, both cis- and trans-isomers (i.e., diastereomers) are within the scope of this invention.

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, phosphorus, fluorine, and chlorine, such as $^2$H, $^3$H, $^{11}$C, $^{13}$C, $^{13}$N, $^{15}$N, $^{18}$O, $^{35}$S, $^{31}$P, $^{33}$P, $^{18}$F and $^{37}$Cl, respectively.

Compounds of the present invention, prodrugs thereof, and pharmaceutically acceptable salts of said compounds, or of said prodrugs which contain the aforementioned isotopes and/or other isotopes of other atoms are within the scope of this invention. Certain isotopically labeled compounds of the present invention, for example, those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

The term "alkyl" refers to straight or branched chains of carbon atoms. Exemplary alkyl groups are $C_3$-$C_{10}$ alkyl groups which include methyl, ethyl, propyl, isopropyl, butyl, isobutyl, pentyl, isopentyl, hexyl and the like, including all regioisomeric forms thereof, and straight and branched chain forms thereof. The term "alkyl" is also used to denote straight or branched chains of carbon atoms having one or more carbon-carbon double bonds, such as vinyl, allyl, butenyl and the like, as well as straight and branched chains of carbon atoms having one or more carbon-carbon triple bonds, such as ethynyl, propargyl, butynyl, and the like.

The term "aryl" denotes a cyclic, aromatic hydrocarbon. Examples include phenyl, naphthyl, anthracenyl, phenanthracenyl. Such aryl groups may further be substituted at available positions with H, F, Cl, Br, I, CN, OH, alkoxy, $NO_2$, $NH_2$, NH-alkyl or N-dialkyl.

The terms "alkoxy" and "aryloxy" denote "O-alkyl" and "O-aryl", respectively. The term "cycloalkyl" denotes a cyclic group of carbon atoms, where the ring formed by the carbon atoms may be saturated or may comprise one or more carbon double bonds in the ring. Examples of cycloalkyl groups include cyclopropyl, cyclobutyl, cyclopentyl, cyclohexyl, cycloheptyl, and the like as well as cyclopentenyl, cyclopentadienyl, cyclohexenyl, cyclohexadienyl, and the like. As used herein, the term "cycloalkyl" is also intended to denote a cyclic group comprising at least two fused rings, such as adamantyl, decahydronaphthalinyl, norbornanyl, where the cyclic group may also have one or more carbon-carbon double bonds in one or more rings, such as in bicyclo (4.3.0)nona-3,6(1)-dienyl, dicyclopentadienyl, 1,2,3,4-tetrahydro-naphthalinyl (i.e., tetralinyl), indenyl, and the like.

The term "halogen" represents chloro, fluoro, bromo and iodo.

The term "heteroaryl" denotes a monocyclic or bicyclic aromatic group wherein one or more carbon atoms are replaced with heteroatoms selected from the group consisting of nitrogen, oxygen, and sulfur. If the heteroaryl group contains more than one heteroatom, the heteroatoms may be the same or different. Preferred heteroaryl groups are five- to fourteen-member rings that contain from one to three heteroatoms independently selected from oxygen, nitrogen, and sulfur. Examples of preferred heteroaryl groups include, but are not limited to, benzo[b]thienyl, chromenyl, furyl, imidazolyl, indazolyl, indolizinyl, indolyl, isobenzofuranyl, isoindolyl, isoquinolinyl, isothiazolyl, isoxazolyl, napthylidinyl, oxadiazolyl, oxazinyl, oxazolyl, phthalazinyl, pteridinyl, purinyl, pyranyl, pyrazinyl, pyrazolyl, pyridazinyl, pyridinyl, triazolyl and tetrazolyl, said heteroaryl groups may be further substituted as described above in the definition of aryl.

A "unit dosage form" as used herein is any form that contains a unit dose of the compound of formula I. A unit dosage form may be, for example, in the form of a tablet or a capsule. The unit dosage form may also be in liquid form, such as a solution or suspension.

The compositions of the present invention may be formulated in a conventional manner using one or more pharmaceutically acceptable carriers. Thus, the active compounds of the present invention may be formulated for oral, buckle, intranasal, parenteral (e.g., intravenous, intramuscular or subcutaneous) or rectal administration or in a form suitable for administration by inhalation or insufflations.

For oral administration, the pharmaceutical compositions may take the form of, for example, tablets or capsules prepared by conventional means with pharmaceutically acceptable excipients such as binding agents (e.g., pre-gelatinized maize starch, polyvinylpyrrolidone or hydroxypropyl methylcellulose), fillers (e.g., lactose, microcrystalline cellulose or calcium phosphate); lubricants (e.g., magnesium stearate, talc, or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispensing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichloro-fluoromethane, dichlorotetrachloroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above is from about 0.1 mg/kg to about 100 mg/kg of the active ingredient per unit dose which could be administered, for example, one to four times per day. Toxicity concerns at the higher level may restrict intravenous (i.v.) dosages to a lower level, such as up to 10 mg/kg. A dose of about 0.1 mg/kg to about 100 mg/kg may be employed for oral (p.o.) administration. Typically, a dosage from about 0.1 mg/kg to about 10 mg/kg may be employed for intramuscular (i.m.) injection. Preferred dosages are in the 1.0 mg/kg to about 100 mg/kg range, and more preferably in the 5 mg/kg to about 50 mg/kg range for i.v. or p.o. administration. The duration of the treatment is usually once per day for a period of one days to three weeks, or until the condition is essentially brought under control.

Aerosol formulations for treatment of the conditions referred to above in the average human are preferably arranged such that each metered dose or "puff" of aerosol contains 0.1 micrograms to 100 micrograms of the active compound of the invention. The overall daily dose with an aerosol will be within the range of 0.1 mg/kg to about 100 mg/kg, and preferably in the range of 1.0 mg/kg to about 25 mg/kg. Administration may be several times daily, for example 2, 3, 4 or 8 times, giving for example 1, 2 or 3 doses each time.

As an example, the mammal in need of treatment or prevention may be a human. As another example, the mammal in need of treatment or prevention may be a mammal other than a human.

A compound of formula I which is basic in nature is capable of forming a wide variety of different salts with various inorganic and organic acids. The acid additions salts are readily prepared by treating the base compounds with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid salts of the active compound used in formulating the pharmaceutical composition of this invention that are basic in nature are those which form non-toxic acid addition salts, e.g., salts containing pharmacologically acceptable anions. Non-limiting examples of the salts include the acetate, benzoate, beta-hydroxybutyrate, bisulfate, bisulfite, bromide, butyne-1,4-dioate, caproate, chloride, chlorobenzoate, citrate, dihydrogen phosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, monohydrogen phosphate, naphthalene-1-sulfonate, naphthalene-2-sulfonate, oxalate, phenylbutyrate, phenylpropionate, phosphate, phthalate, phenylacetate, propanesulfonate, propiolate, propionate, pyrophosphate, pyrosulfate, sebacate, suberate, succinate, sulfate, sulfite, sulfonate, tartrate, xylenesulfonate, acid phosphate, acid citrate, bitartrate, succinate, gluconate, saccharate, nitrate, methanesulfonate, and pamoate {i.e., 1,1'-methylene-bis-(2-hydroxy-3-naphthoate)] salts.

Also included within the scope of this invention are solvates and hydrates of compounds of formula I and their pharmaceutically acceptable salts. The present invention includes within its scope all possible stoichiometric and non-stoichiometric forms.

In the examples that follow, the abbreviations used in this document are intended to have the following, general meaning:

bm: broad multiplet (NMR)
bs: broad singlet (NMR)
d: doublet (NMR)
dd: doublet of doublets (NMR)
d.e.: diatomaceous earth, filtering agent
calcd.: calculated value
J: coupling constant (NMR)
LC: high pressure liquid chromatography (HPLC)
m: multiplet (NMR)
min: minute(s)
m/z: mass to charge ratio (mass spectroscopy)
obsd: observed value
Rf: retention factor (chromatography)
RT: retention time (chromatography)
rt: room temperature (typically 25° C.)
s: singlet (NMR)
t: triplet (NMR),
T: temperature
tlc: thin layer chromatography
TFA: trifluoroacetic acid
THF: tetrahydrofuran Solvents were purchased and used without purification. Yields were calculated for material judged to be homogeneous by thin layer chromatography and NMR. Thin layer chromatography was performed on Kieselgel plates eluting with the indicated solvents, visualized by using a 254 nm UV lamp, and stained with either an aqueous $KMnO_4$ solution or an ethanolic solution of 12-molybdophosphoric acid.

Nuclear Magnetic Resonance (NMR) spectra were acquired on a 400 MHz NMR Spectrometer. Chemical shifts for proton $^1$H-NMR spectra are reported in parts per million (ppm) relative to the singlet of $CDCl_3$ at 7.24 ppm.

Preparative Conditions for Chromatographic Purification and Analysis.

Instrument: LaChrom HPLC system (Merck-Hitachi) for UV-directed purification and Waters HPLC/MS for mass directed purification, both equipped with RP $C_{18}$ column (Phenomenex Gemini NX 5µ 150 mm×30 mm).

Eluent I:
A: Acetonitrile-$H_2O$=5:95, 10 mM $NH_4HCO_3$ buffer, pH 8.0
B: Acetonitrile-$H_2O$=80:20 10 mM $NH_4HCO_3$ buffer, pH 8.0

Eluent II:
A: Acetonitrile-$H_2O$=5:95, 20 mM $HCOONH_4/NH_4OH$ buffer, pH 7.4
B: Acetonitrile-$H_2O$=80:20, 20 mM $HCOONH_4/NH_4OH$ buffer, pH 7.4

Eluent III:
A: Acetonitrile-$H_2O$=5:95, 20 mM $CH_3COONH_4/CH_3COOH$ buffer, pH 6
B: Acetonitrile-$H_2O$=80:20, 20 mM $CH_3COONH_4/CH_3COOH$ buffer, pH 6

Eluent IV:
A: $H_2O$ with 0.1% TFA, pH 2.2
B: Acetonitrile with 0.1% TFA, pH 2.2

Gradient program: adjusted according to the compound properties
Column Temp.: room temperature (25° C.)
Flow Rate: up to 40 ml/min
Detection and triggering: UV detector (220 nm)
Conditions for LC-MS analysis:
Column: Zorbax RRHD Eclipse XDB (Agilent) $C_{18}$, 1.9 micron, 50 mm×2.1 mm.
Eluent I:
A: Acetonitrile-$H_2O$=5:95, 20 mM $HCOONH_4$/$NH_4OH$ buffer, pH 7.4
B: Acetonitrile-$H_2O$=80:20, 20 mM $HCOONH_4$/$NH_4OH$ buffer, pH 7.4
Eluent I:
A: $H_2O$ with 0.1% TFA, pH 2.2
B: Acetonitrile with 0.1% TFA, pH 2.2
Gradient program: adjusted according to the compound properties; typically, start: 0% B to 100% B in 1 minute, 0.8 minute isocratic B.
Column Temp.: 40° C.
Flow Rate: 0.6 mL/min
Sample Conc.: ca. 1 mg/mL
Sample Solvent: Acetonitrile
Injection: 0.5 μL
Detection wavelength: 220 nm
MS conditions:
Measured Mass Range: 100-750 Daltons
Scan Time: 0.2 s
Ion mode: ES±
Cone Voltage: 20 V
Capillary Voltage: 3 V
Source temp.: 140° C.
Desolvation temp.: 450° C.
Desolvation gas: 450 L/h
Cone gas: 60 L/h

EXAMPLE 1

General Procedure A

Trans-1-(2-chlorophenyl)-$N^2$-(2-(dimethylamino) ethyl)-$N^1$-methylcyclohexane-1,2-diamine (1a) and Cis-1-(2-chlorophenyl)-$N^2$-(2-(dimethylamino) ethyl)-$N^1$-methylcyclohexane-1,2-diamine (1b)

A mixture of 2-(2-chlorophenyl)-2-(methylamino)cyclohexanone hydrochloride (ketamine HCl) (423 mg, 1.54 mmol) and $N^1$,$N^1$-dimethylethane-1,2-diamine (1.6 mL, 19.2 mmol) was heated at 110° C. for 20 h. The mixture was cooled to room temperature and sodium cyano-borohydride (490 mg, 7.8 mmol) was added. The mixture was then heated at 110° C. overnight. The cooled reaction mixture was quenched with saturated $NaHCO_3$, extracted with $CH_2Cl_2$ (75 mL), dried ($Na_2SO_4$) and concentrated to dryness to give 500 mg of crude product (M/Z 310 [$M^+$+H]). This material was further purified by column chromatography, as described in Method A above.

a.) The product fractions, (RT=0.50) were combined, the solvents were removed and the trans-isomer was isolated as a trifluoroacetate salt, 0.149 g.
MS: calcd. for $C_{17}H_{28}ClN_3$: 309.9; obsd.: 309.2 (m+1).
$^1$H-nmr (DMSO-$d_6$, 400 MHz, T=30° C.) δ 1.4-1.7 (m, 3H), 1.75-2.0 (m, 3H), 2.10-2.35 (m+s, 5H), 2.40-2.50 (m+s, 6H), 2.75-2.85 (m, 2H), 2.92 (m, 1H), 3.15 (m, 1H), 7.40-7.50 (m, 2H), 7.55-7.65 (m, 2H), 8.5 (bs, 1H).

b.) The more polar fractions (RT=0.64) were separately combined and, after removal of the solvents, the cis-isomer was isolated as a solid, 0.078 g.
MS: calcd. for $C_{17}H_{28}ClN_3$: 309.9; obsd.: 309.19 (m+1).

The following compounds were also prepared using the general procedure A, as described above for the title compounds of Examples 1:

EXAMPLE 2

Trans-1-(2-chlorophenyl)-$N^2$-cyclopropylmethyl-$N^1$-methylcyclohexane-1,2-diamine (2a), and Cis-1-(2-chlorophenyl)-$N^2$-cyclopropylmethyl-$N^1$-methylcyclohexane-1,2-diamine (2b)

The title compounds of Example 2 were prepared according to general procedure A using cyclopropylmethanamine and ketamine.

a.) LC (RT=0.55)/Mass spectrum (m/z) calcd. for $C_{17}H_{25}ClN_2$: 292.8; obsd.: 293 (M+1, 100%), 295 (M+1, 37Cl, 30%), 262 (28%).
$^1$H-nmr (DMSO-$d_6$, 400 MHz, T=30° C.) δ 0.1 (m, 2H), 0.2 (m, 2H), 0.5 (m, 2H), 0.85 (m, 1H), 1.50 (m, 2H), 1.65 (d, 1H), 1.85-2.10 (m, 2H), 2.05 (s, 3H), 2.15 (m, 2H), 2.30-2.55 (m, 2H), 2.70 (dd, 1H), 4.45 (s, 1H), 7.40-7.65 (m, 4H).

b.) LC (RT=0.72)/MS: calcd. for $C_{17}H_{25}ClN_2$: 292.8; obsd.: 293 (M+1).
$^1$H-nmr (DMSO-d6, 400 MHz, T=30° C.) δ 0.30 (m, 2H), 0.55 (dd, 2H), 1.0 (m, 1H), 1.2 (m, 1H), 1.40-1.85 (m, 5H), 2.05 (m+s, 4H), 2.80 (m, 3H), 4.20 (m, 1H), 6.5 (bs, 2H), 7.35-7.50 (m, 2H), 7.52 (dd, 1H), 7.64 (d, 1H).

EXAMPLE 3

Trans-1-(2-chlorophenyl)-$N^2$-cyclopentyl-$N^1$-methylcyclohexane-1,2-diamine (3a), and Cis-1-(2-chlorophenyl)-$N^2$-cyclopentyl-$N^1$-methylcyclohexane-1,2-diamine (3b)

The title compounds of Example 3 were prepared according to general procedure A using cyclopentylamine and ketamine.

a.) LC (RT=0.58)/MS: calcd. for $C_{18}H_{27}ClN_2$: 306.9; obsd.: 306.19 (m+1).

b.) LC (RT=0.96)/MS: calcd. for $C_{18}H_{27}ClN_2$: 306.9; obsd.: 306.19 (m+1).

EXAMPLE 4

Trans-1-(2-chlorophenyl)-$N^2$-(3-methoxypropyl)-$N^1$-methylcyclohexane-1,2-diamine (4a), and Cis-1-(2-chlorophenyl)-$N^2$-(3-methoxypropyl)-$N^1$-methylcyclohexane-1,2-diamine (4b)

The title compounds of Example 4 were prepared according to general procedure A using 3-methoxypropylamine and ketamine.

a.) LC (RT=0.59)/MS: calcd. for $C_{17}H_{27}ClN_2O$: 310.9; obsd.: 310.18 (m+1).

b.) LC (RT=0.67)/MS: calcd. for $C_{17}H_{27}ClN_2O$: 310.9; obsd.: 310.18 (m+1).

EXAMPLE 5

Trans-1-(2-chlorophenyl)-N$^1$-methyl-N$^2$-(tetrahydrofuran-2-ylmethyl)cyclohexane-1,2-diamine (5a), and Cis-1-(2-chlorophenyl)-N$^1$-methyl-N$^2$-(tetrahydrofuran-2-ylmethyl)cyclohexane-1,2-diamine (5b)

The title compounds of Example 5 were prepared according to general procedure A using 2-aminomethyl-2,3,4,5-tetrahydrofuran and ketamine.
  a.) LC (RT=0.63)/MS: calcd. for $C_{18}H_{27}ClN_2O$: 322.9; obsd.: 322.18 (m+1).
  b.) LC (RT=0.70)/MS: calcd. for $C_{18}H_{27}ClN_2O$: 322.9; obsd.: 322.18 (m+1).

EXAMPLE 6

Cis-1-(2-chloropheny)-N$^2$-(3-(dimethylamino)propyl) N$^1$-methyl-cyclohexane-1,2-diamine (6)

The title compound of Example 6 was prepared according to general procedure A using 3-(N,N-dimethylamino)-propylamine and ketamine.
  LC (RT=0.66)/MS: calcd. for $C_{18}H_{30}ClN_3$: 323.9; obsd.: 323.21 (m+1).

EXAMPLE 7

Trans-N$^2$-benzyl-1-(2-chlorophenyl)-N$^1$-methylcyclohexane-1,2-diamine (7a) and Cis-N$^2$-benzyl-1-(2-chlorophenyl)-N$^1$-methylcyclohexane-1,2-diamine (7b)

The title compounds of Example 7 were prepared according to general procedure A using benzylamine and ketamine.
  a.) LC (RT=0.66)/MS: calcd. for $C_{20}H_{25}ClN_2$: 328.9; obsd.: 328.17 (m+1).
  b.) LC (RT=1.01)/MS: calcd. for $C_{20}H_{25}ClN_2$: 328.9; obsd.: 328.17 (m+1).

EXAMPLE 8

Cis-1-(2-chlorophenyl)-N$^1$-methyl-N$^2$-(pyridin-4-ylmethyl)cyclohexane-1,2-diamine (8)

The title compound of Example 8 was prepared according to general procedure A using 4-(aminomethyl)-pyridine and ketamine.
  LC (RT=0.70)/MS: calcd. for $C_{19}H_{24}ClN_3$: 329.9; obsd.: 329.17 (m+1).

EXAMPLE 9

Trans-1-(2-chlorophenyl)-N$^1$-methyl-N$^2$-(pyridin-3-ylmethyl)cyclohexane-1,2-diamine (9)

The title compound of Example 9 was prepared according to general procedure A using 3-(aminomethyl)-pyridine and ketamine.
  LC (RT=0.56)/MS: calcd. for $C_{19}H_{23}ClN_3$: 329.9; obsd.: 329.17 (m+1).

EXAMPLE 10

Cis-1-(2-chlorophenyl)-N$^2$-(1-(R)-phenyl)-ethyl)-N$^1$-methylcyclohexane-1,2-diamine (10)

The title compound of Example 10 was prepared according to general procedure A using (R)-α-methyl-benzylamine and ketamine.
  LC (RT=1.05)/MS: calcd. for $C_{21}H_{27}ClN_2$: 342.9; obsd.: 342.19 (m+1).

EXAMPLE 11

Trans-1-(2-chlorophenyl)-N$^2$-(1-(S)-phenyl)-ethyl)-N$^1$-methylcyclohexane-1,2-diamine (11)

The title compound of Example 11 was prepared according to general procedure A using (S)-α-methyl-benzylamine and ketamine.
  LC (RT=0.81)/MS: calcd. for $C_{21}H_{27}ClN_2$: 342.9; obsd.: 342.19 (m+1).

EXAMPLE 12

Trans-1-(2-chlorophenyl)-N$^2$-(3-(1-imidazolyl)-propyl)-N$^1$-methylcyclohexane-1,2-diamine (12a), and Cis-1-(2-chlorophenyl)-N$^2$-(3-(1-imidazolyl)-propyl)-N$^1$-methylcyclohexane-1,2-diamine (12b)

The title compounds of Example 12 were prepared according to general procedure A using 3-(1-imidazolyl)-propylamine and ketamine.
  a.) LC (RT=0.70)/MS: calcd. for $C_{19}H_{27}ClN_4$: 346.9; obsd.: 346.19 (m+1).
  $^1$H-nmr (DMSO-d6, 400 MHz, T=30° C.) δ 1.35-1.55 (m, 2H), 1.60-1.75 (m, 1H), 1.80-2.00 (m, 4H), 2.05-2.35 (m+s, 6H), 2.45-2.70 (m, 2H), 3.95-4.25 (m, 3H), 7.40-7.50 (m, 3H), 7.55 (m, 1H), 7.60 (m, 1H), 7.70 (s, 1H), 8.95 (s, 1H).
  b.) LC (RT=0.54)/MS: calcd. for $C_{19}H_{27}ClN_4$: 346.9; obsd.: 346.19 (m+1).
  $^1$H-nmr (DMSO-d6, 400 MHz, T=30° C.) δ 1.25 (bs, 1H), 1.40 (bs, 1H), 1.50-1.80 (m, 4H), 1.90 (m, 1H), 2.00-2.25 (m+s, 5H), 2.55 (m, 1H), 2.70-2.95 (m, 2H), 3.90 (bs, 1H), 4.20-4.35 (m, 2H), 6.50 (bs, 2H), 7.40-7.45 (m, 2H), 7.52 (m, 1H), 7.65 (m, 1H), 7.70 (m, 1H), 7.75 (m, 1H), 9.10 (s, 1H).

EXAMPLE 13

Trans-1-(2-chlorophenyl)-N$^2$-(1-ethyl-pyrrolidin-2-ylmethyl)-N$^1$-methylcyclohexane-1,2-diamine (13a), and Cis-1-(2-chlorophenyl)-N$^2$-(1-ethyl-pyrrolidin-2-ylmethyl)-N$^1$-methylcyclohexane-1,2-diamine (13b)

The title compounds of Example 13 were prepared according to general procedure A using N-ethyl-2-(aminomethyl)-pyrrolidine and ketamine.
  a.) LC (RT=0.55)/MS: calcd. for $C_{20}H_{32}ClN_3$: 349.9; obsd.: 349.23 (m+1).
  b.) LC (RT=0.70)/MS: calcd. for $C_{20}H_{32}ClN_3$: 349.9; obsd.: 349.23 (m+1).

EXAMPLE 14

Trans-1-(2-chlorophenyl)-N$^2$-(3-(pyrrolidin-1-yl) propyl)-N$^1$-methylcyclohexane-1,2-diamine (14a), and Cis-1-(2-chlorophenyl)-N$^2$-(3-(pyrrolidin-1-yl) propyl)-N$^1$-methylcyclohexane-1,2-diamine (14b)

The title compounds of Example 14 were prepared according to general procedure A using N-(3-aminopropyl)-pyrrolidine and ketamine.
  a.) LC (RT=0.50)/MS: calcd. for $C_{20}H_{32}ClN_3$: 349.9; obsd.: 349.23 (m+1).

b.) LC (RT=0.68)/MS: calcd. for $C_{20}H_{32}ClN_3$: 349.9; obsd.: 349.23 (m+1).

EXAMPLE 15

Trans-1-(2-chlorophenyl)-$N^2$-(3-phenylpropyl)-$N^1$-methylcyclohexane-1,2-diamine (15a), and Cis-1-(2-chlorophenyl)-$N^2$-(3-phenylpropyl)-$N^1$-methylcyclohexane-1,2-diamine (15b)

The title compounds of Example 15 were prepared according to general procedure A using 3-aminopropylbenzene and ketamine.

a.) LC (RT=0.71)/MS: calcd. for $C_{22}H_{29}ClN_2$: 356.9; obsd.: 356.19 (m+1).

b.) LC (RT=0.77)/MS: calcd. for $C_{22}H_{29}ClN_2$: 356.9; obsd.: 356.19 (m+1).

EXAMPLE 16

Trans-1-(2-chlorophenyl)-$N^2$-(3-(morpholin-1-yl)propyl)-$N^1$-methylcyclohexane-1,2-diamine (16a), and Cis-1-(2-chlorophenyl)-$N^2$-(3-(morpholin-1-yl)propyl)-$N^1$-methylcyclohexane-1,2-diamine (16b)

The title compounds of Example 16 were prepared according to general procedure A using N-(3-aminopropyl)-morpholine and ketamine.

a.) LC (RT=0.49)/MS: calcd. for $C_{20}H_{32}ClN_3O$: 365.9; obsd.: 365.22 (m+1).

b.) LC (RT=0.86)/MS: calcd. for $C_{20}H_{32}ClN_3O$: 365.9; obsd.: 365.22 (m+1).

EXAMPLE 17

Trans-1-(2-chlorophenyl)-$N^2$-(3-(4-methylpiperazin-1-yl)propyl)-$N^1$-methylcyclohexane-1,2-diamine (17a), and Cis-1-(2-chlorophenyl)-$N^2$-(3-(4-methylpiperazin-1-yl)propyl)-$N^1$-methylcyclohexane-1,2-diamine (17b)

The title compounds of Example 17 were prepared according to general procedure A using $N^1$-methyl-$N^2$-(3-aminopropyl)-piperazine and ketamine.

a.) LC (RT=0.48)/MS: calcd. for $C_{21}H_{35}ClN_4$: 378.9; obsd.: 378.26 (m+1).

b.) LC (RT=0.69)/MS: calcd. for $C_{21}H_{35}ClN_4$: 378.9; obsd.: 378.26 (m+1).

EXAMPLE 18

Trans-1-(2-chlorophenyl)-$N^2$-cyclohexyl-$N^1$-methylcyclohexane-1,2-diamine (18a), and Cis-1-(2-chlorophenyl)-$N^2$-cyclohexyl-$N^1$-methylcyclohexane-1,2-diamine (18b)

The title compounds of Example 18 were prepared according to general procedure A using cyclohexylamine and ketamine.

a.) LC (RT=1.55)/MS: calcd. for $C_{19}H_{29}ClN_2$: 320.9; obsd.: 320.19 (m+1).

b.) LC (RT=1.05)/MS: calcd. for $C_{19}H_{29}ClN_2$: 320.9; obsd.: 320.19 (m+1).

EXAMPLE 19

General Procedure B

Cis-(1R,2R)-1-(2-chlorophenyl)-$N^2$-(3-phenylpropyl)-$N^1$-methylcyclohexane-1,2-diamine (19a), and Cis-(1S,2S)-1-(2-chlorophenyl)-$N^2$-(3-phenylpropyl)-$N^1$-methylcyclohexane-1,2-diamine (19b)

The title compound of Example 15b (110 mg) was purified using high pressure liquid chromatography (HPLC) under the following conditions:

Instrument: JASCO-SFC (SuperCritical Fluid Chromatography) Semi-Prep HPLC (JASCO Inc., Easton, Md., USA).

Stationary Phase: Diacel Chiralpak AS-H, 10 mm column.

Mobile Phase: Ethanol/$CO_2$. Isocratic 5% EtOH/95% $CO_2$.

Detection: UV detection at 220, 254 nM.

Column Temp.: 25° C.

Flow Rate: 2.5 mL/min

Fraction 1 (19a): 35 mg. RT=7.187 min, ee>99%, purity >98%.

Fraction 2 (19b): 30 mg. RT=8.347 min, ee>99%, purity >95%. Mass Spectrum: (ESI$^+$ scan) 357.2 ($M_{35Cl}$+H)$^+$, 359 ($M_{37Cl}$+H)$^+$.

EXAMPLE 20

Cis-(1R,2R)-1-(2-chlorophenyl)-$N^2$-(3-(morpholin-1-yl)propyl)-$N^1$-methylcyclohexane-1,2-diamine (20a), and Cis-(1S,2S)-1-(2-chlorophenyl)-$N^2$-(3-(morpholin-1-yl)propyl)-$N^1$-methylcyclohexane-1,2-diamine (20b)

The title compound of Example 16b (60 mg) was purified using high pressure liquid chromatography (HPLC) under the conditions described in Example 19 above.

Fraction 1 (20a): 17 mg. RT=10.192 min, ee>99%, purity >99%.

Mass Spec (ESI+, Acquisition Time=2.546 min): m/z=366.23 (100%, (M+H)$^+$), 368 (33%, (M+H)$^+$ for Cl$^{37}$)

Fraction 2 (20b): 18 mg. RT=12.783 min, ee>99%, purity >99%.

Mass Spec (ESI+, Acquisition Time=2.548 min): m/z=366.23 (100%, (M+H)$^+$), 368 (33%, (M+H)$^+$ for Cl$^{37}$).

Determination of Pharmacological Activity

The compounds from the above Examples were tested for Sigma-1 activity. Ki determinations were generously provided by the National Institute of Mental Health's Psychoactive Drug Screening Program (PDSP), Contract # HHSN-271-2013-00017-C (NIMH PDSP). The NIMH PDSP is Directed by Bryan L. Roth MD, PhD at the University of North Carolina at Chapel Hill and Project Officer Jamie Driscoll at NIMH, Bethesda Md., USA. Procedures employed by the PDSP are described in the NIMH PDSP Assay Protocol Book, Version II.

| Data | |
|---|---|
| Example | Sigma-1 KI (nM) |
| 12b | 231 |
| 15a | 2260 |
| 15b | 177 |
| 16b | 17 |
| 17a | 19 |
| 17b | 72 |

The invention claimed is:

1. A method of treating a disease or disorder, selected from the group consisting of stroke, Huntington's disease and amyotrophic lateral sclerosis (ALS), comprising administering to a mammal in need of said treatment an effective amount of a compound of the formula (I):

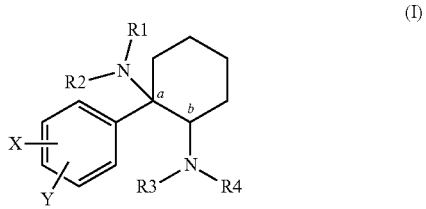

(I)

or the pharmaceutically acceptable salt(s) thereof, wherein:
X and Y are independently selected from the group consisting of H, F, Cl, Br, I, CN, OH, $CF_3$, $C_2F_5$, $C_1$-$C_6$-alkyl, $C_3$-$C_7$-cycloalkyl, $C_1$-$C_3$-alkoxy, aryl, heteroaryl, —(—C=O)—R5, —NH—(C=O)—R5, —NR5-(C=O)—R6, —(C=O)—NHR5 and —(C=O)—NR5R6
R1 is hydrogen;
R2 is hydrogen or $C_1$-$C_6$-alkyl;
R3 is hydrogen or $C_1$-$C_6$-alkyl;
R4 is selected from the group consisting of $C_1$-$C_6$-alkyl, $C_3$-$C_7$-cycloalkyl and $(CH_2)_n$-R7, or
NR3R4 is a 5- to 12-membered cyclic or bicyclic ring system containing up to two additional heteroatoms in the ring, selected from N, O and S;
R5 is selected from $C_1$-$C_6$-alkyl and aryl;
R6 is selected from $C_1$-$C_6$-alkyl and aryl, or
NR5R6 is a 5- to 12-membered cyclic or bicyclic ring system containing up to two additional heteroatoms in the ring, selected from N, O and S;
R7 is independently selected from the group consisting of H, $C_1$-$C_6$-alkyl, $C_3$-$C_7$-cycloalkyl, ($C_1$-$C_6$-alkyloxy)-, ($C_1$-$C_6$-alkyloxy)-($C_1$-$C_6$-alkyl)-, NR8R9-, NR8R9-($C_1$-$C_6$-alkyl), aryl, heterocyclyl and heteroaryl; and
R8 and R9 are independently selected from hydrogen, $C_1$-$C_6$-alkyl and aryl, or taken together with the N atom to which they are attached form a 3- to 8-membered ring containing up to two additional heteroatoms, selected from N, O and S; and
n is an integer between 0 and 6.

2. The method of claim 1 comprising administering a pharmaceutical composition comprising a compound of formula (I), or a pharmaceutically acceptable salt thereof, and a pharmaceutically acceptable carrier.

3. The method of claim 1 wherein R4 is $C_1$-$C_6$-alkyl, $C_3$-$C_7$-cycloalkyl or $(CH_2)_n$-R7 and wherein n is an integer between 0 and 6.

4. The method of claim 1 wherein R7 is independently selected from the group consisting of H, $C_1$-$C_6$-alkyl, $C_3$-$C_7$-cycloalkyl, ($C_1$-$C_6$-alkyloxy)-($C_1$-$C_6$-alkyl)-, NR8R9-, NR8R9-($C_1$-$C_6$-alkyl)-, aryl, heterocyclyl and heteroaryl.

5. The method of claim 1 wherein said compound is selected from:
trans-1-(2-chlorophenyl)-$N^2$-(2-(dimethylamino)ethyl)-$N^1$-methylcyclo-hexane-1,2-diamine;
cis-1-(2-chlorophenyl)-$N^2$-(2-(dimethylamino)ethyl)-$N^1$-methylcyclo-hexane-1,2-diamine;
trans-1-(2-chlorophenyl)-$N^2$-cyclopropyl-$N^1$-methylcyclohexane-1,2-diamine;
cis-1-(2-chlorophenyl)-$N^2$-cyclopropyl-$N^1$-methylcyclohexane-1,2-diamine;
trans-1-(2-chlorophenyl)-$N^2$-cyclopentyl-$N^1$-methylcyclohexane-1,2-diamine;
cis-1-(2-chlorophenyl)-$N^2$-cyclopentyl-$N^1$-methylcyclohexane-1,2-diamine;
trans-1-(2-chlorophenyl)-$N^2$-(3-methoxypropyl)-$N^1$-methylcyclohexane-1,2-diamine;
cis-1-(2-chlorophenyl)-$N^2$-(3-methoxypropyl)-$N^1$-methylcyclohexane-1,2-diamine;
trans-1-(2-chlorophenyl)-$N^1$-methyl-$N^2$-(tetrahydrofuran-2-ylmethyl)cyclohexane-1,2-diamine;
cis-1-(2-chlorophenyl)-$N^1$-methyl-$N^2$-(tetrahydrofuran-2-ylmethyl)cyclohexane-1,2-diamine;
cis-1-(2-chloropheny)-$N^2$-(3-(dimethylamino)propyl)-$N^1$-methylcyclohexane-1,2-diamine;
trans-$N^2$-benzyl-1-(2-chlorophenyl)-$N^1$-methylcyclohexane-1,2-diamine;
cis-$N^2$-benzyl-1-(2-chlorophenyl)-$N^1$-methylcyclohexane-1,2-diamine;
cis-1-(2-chlorophenyl)-$N^1$-methyl-$N^2$-(pyridin-4-ylmethyl)cyclohexane-1,2-diamine;
trans-1-(2-chlorophenyl)-$N^1$-methyl-$N^2$-(pyridin-3-ylmethyl)cyclohexane-1,2-diamine;
cis-(2-chlorophenyl)-$N^2$-(1-(R)-phenyl)-ethyl)-$N^1$-methylcyclohexane-1,2-diamine;
trans-(2-chlorophenyl)-$N^2$-(1-(S)-phenyl)-ethyl)-$N^1$-methylcyclohexane-1,2-diamine;
trans-(2-chlorophenyl)-$N^2$-(3-(1-imidazolyl)-propyl)-$N^1$-methylcyclohexane-1,2-diamine;
cis-(2-chlorophenyl)-$N^2$-(3-(1-imidazolyl)-propyl)-$N^1$-methylcyclohexane-1,2-diamine;
trans-(2-chlorophenyl)-$N^2$-(1-ethyl-pyrrolidin-2-ylmethyl)-$N^1$-methylcyclohexane-1,2-diamine;
cis-(2-chlorophenyl)-$N^2$-(1-ethyl-pyrrolidin-2-ylmethyl)-$N^1$-methylcyclohexane-1,2-diamine;
trans-(2-chlorophenyl)-$N^2$-(3-(pyrrolidin-1-yl)propyl)-$N^1$-methylcyclohexane-1,2-diamine;
cis-(2-chlorophenyl)-$N^2$-(3-(pyrrolidin-1-yl)propyl)-$N^1$-methylcyclohexane-1,2-diamine;
trans-1-(2-chlorophenyl)-$N^2$-(3-phenylpropyl)-$N^1$-methylcyclohexane-1,2-diamine;
cis-(2-chlorophenyl)-$N^2$-(3-phenylpropyl)-$N^1$-methylcyclohexane-1,2-diamine;
trans-1-(2-chlorophenyl)-$N^2$-(3-(morpholin-1-yl)propyl)-$N^1$-methylcyclohexane-1,2-diamine;
cis-1-(2-chlorophenyl)-$N^2$-(3-(morpholin-1-yl)propyl)-$N^1$-methylcyclohexane-1,2-diamine;
trans-1-(2-chlorophenyl)-$N^2$-(3-(4-methylpiperazin-1-yl)propyl)-$N^1$-methylcyclohexane-1,2-diamine;
cis-1-(2-chlorophenyl)-$N^2$-(3-(4-methylpiperazin-1-yl)propyl)-$N^1$-methylcyclohexane-1,2-diamine;
trans-1-(2-chlorophenyl)-$N^2$-cyclohexyl- $N^1$-methylcyclohexane-1,2-diamine; and cis-1-(2-chlorophenyl)-N$^2$-(2-(dimethylamino)ethyl)-N$^1$-methylcyclohexane-1,2-diamine.

6. The method of claim 1 wherein the compound is selected from the group consisting of:

1-(2-chloro-4-methoxyphenyl)-N$^2$-[3-(4,5-dimethyl-1H-imidazol-2-yl)propyl]-N$^1$-methyl-cyclohexane-1,2-diamine;

1-(2-chlorophenyl)-N$^1$-methyl-N$^2$-[3-(1H-1,2,4-triazol-5-yl)propyl]-cyclohexane-1,2-diamine;

1-(2-methylphenyl)-N$^1$-methyl-N$^2$-[3-(3-methyl-1H-1,2,4-triazol-5-yl)propyl]-cyclohexane-1,2-diamine;

1-(2,4-dichlorophenyl)-N$^1$-methyl-N$^2$-[3-(1H-tetrazol-5-yl)propyl]-cyclohexane-1,2-diamine;

1-(3,4-fluorophenyl)-N$^1$-methyl-N$^2$-[2-(1-methyl-1H-tetrazol-5-yl)ethyl]-cyclohexane-1,2-diamine;

1-(4-chlorophenyl)-N$^2$-(2-(dimethylamino)ethyl)-N$^1$-methylcyclohexane-1,2-diamine;

1-(2,4-dichlorophenyl)-N$^2$-(2-(dimethylamino)ethyl)-N$^1$-methylcyclohexane-1,2-diamine;

1-(3,4-difluorophenyl)-N$^2$-(2-(dimethylamino)ethyl)-N$^1$-methylcyclohexane-1,2-diamine;

1-(4-isopropylphenyl)-N$^2$-(2-(dimethylamino)ethyl)-N$^1$-methylcyclohexane-1,2-diamine;

1-(2-methoxyphenyl)-N$^2$-(2-(dimethylamino)ethyl)-N$^1$-methylcyclohexane-1,2-diamine;

1-(2-chlorophenyl)-N$^2$-(2-(dimethylamino)ethyl)-N$^1$-methylcyclohexane-1,2-diamine;

1-(2-chlorophenyl)-N$^2$-[3-(1H-imidazol-2-yl)propyl]-N$^1$-methylcyclohexane-1,2-diamine;

1-(2-chlorophenyl)-N$^2$-[2-(1H-imidazol-2-yl)ethyl]-N$^1$-methylcyclohexane-1,2-diamine;

1-(2-chlorophenyl)-N$^1$-methyl-N$^2$-[3-(1,3-thiazol-2-yl)propyl]-cyclohexane-1,2-diamine;

1-(3,5-dimethyl-2-chlorophenyl)-N$^1$-methyl-N$^2$-[3-(1,3-thiazol-2-yl)propyl]-cyclohexane-1,2-diamine;

1-(3,5-dimethyl-phenyl)-N$^1$-methyl-N$^2$-[3-(4,5-dimethyl-1,3-thiazol-2-yl)propyl]-cyclohexane-1,2-diamine;

1-(2-chlorophenyl)-N$^2$-[3-(1,3-benzothiazol-2-yl)propyl]-N$^1$-methylcyclohexane-1,2-diamine;

1-(2,3-dichlorophenyl)-N$^2$-[3-(1,3-benzimidazol-2-yl)propyl]-N$^1$-methylcyclohexane-1,2-diamine;

1-(3,4-dichlorophenyl)-N$^2$-(2-(3,4-difluorophenypethyl)-N$^1$-methylcyclohexane-1,2-diamine;

1-(2-chlorophenyl)-N$^2$-(3-(3,4-difluorophenyl)propyl)-N$^1$-methylcyclohexane-1,2-diamine;

1-(2-chlorophenyl)-N$^2$-(3-(4-fluorophenyl)propyl)-N$^1$-methylcyclohexane-1,2-diamine;

1-(2-chlorophenyl)-N$^2$-(3-(3,4-dichlorophenyl)propyl)-N$^1$-methylcyclohexane-1,2-diamine;

1-(2-chlorophenyl)-N$^2$-(3-(3,4-dimethoxyphenyl)propyl)-N$^1$-methylcyclohexane-1,2-diamine;

1-(2-chlorophenyl)-N$^2$-[(4,5-dimethyl-1H-imidazol-2-yl)methyl]-N$^1$-ethylcyclohexane-1,2-diamine and 1-(2-chlorophenyl)-N$^1$-ethyl-N$^2$-[(1-methyl-1H-imidazol-2-yl)methyl]cyclohexane-1,2-diamine.

\* \* \* \* \*